United States Patent [19]

Sandefur et al.

[11] Patent Number: 4,620,002

[45] Date of Patent: Oct. 28, 1986

[54] 2-PYRIMIDYL ALKANESULFONATES

[75] Inventors: Louise O. Sandefur; Wojciech Slusarek, both of Rochester; Burton D. Wilson, Webster; Cataldo A. Maggiulli, Pittsford, all of N.Y.

[73] Assignee: Eastman Kodak Company, Rochester, N.Y.

[21] Appl. No.: 407,223

[22] Filed: Aug. 11, 1982

[51] Int. Cl.$^4$ .............................................. C07D 239/34
[52] U.S. Cl. ................... 544/318; 514/252; 544/230; 544/295; 544/296; 544/402
[58] Field of Search ................ 544/295, 318

[56] References Cited

U.S. PATENT DOCUMENTS

| | | |
|---|---|---|
| 2,839,446 | 6/1958 | Margot et al. ............... 544/318 |
| 3,398,151 | 8/1968 | Wu ................................ 544/230 |
| 3,717,634 | 2/1973 | Wu et al. ...................... 424/251 |
| 3,880,852 | 4/1975 | Cole et al. ................... 544/295 |
| 3,907,801 | 9/1975 | Wu et al. ...................... 424/250 |
| 3,975,384 | 8/1976 | Narr et al. .................... 544/295 |
| 3,976,776 | 8/1976 | Wu et al. ...................... 424/251 |
| 4,113,860 | 9/1978 | Maurer et al. ................ 544/318 |

OTHER PUBLICATIONS

Howard et al, *J. Org. Chem.*, vol. 18, pp. 1484–1488, (1953).
Crossland et al, *J. Org. Chem.*, vol. 35, pp. 3195–3196, (1970).

*Primary Examiner*—Glennon H. Hollrah
*Assistant Examiner*—James H. Turnipseed
*Attorney, Agent, or Firm*—Alfred P. Lorenzo

[57] ABSTRACT

Novel 2-pyrimidyl alkanesulfonates are prepared by reacting a 2-hydroxypyrimidine acid salt with an alkanesulfonyl chloride in the presence of an acid acceptor. The novel 2-pyrimidyl alkanesulfonates are advantageously employed to prepare 1-(cyanoalkyl)-4-(2-pyrimidyl)piperazines by reacting them with a novel 1-(cyanoalkyl)piperazine in the presence of an acid acceptor.

2 Claims, No Drawings

2-PYRIMIDYL ALKANESULFONATES

BACKGROUND OF THE INVENTION

1. Field of the Invention

The invention relates to 2-pyrimidyl alkanesulfonates, methods for their preparation, and methods for their use in preparing 1-(cyanoalkyl)-4-(2-pyrimidyl)-piperazines (which are in turn useful materials for producing compounds having pharmacological utility as tranquilizing and anti-emetic agents).

2. Description Relative to the Prior Art

It is known that 8-[w-[4-(2-pyrimidyl)-1-piperazinyl]alkyl]-8-azaspiro[4.5]decane-7,9-diones represented by the structural formula

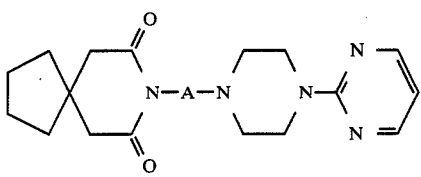

Formula I wherein A represents an alkylene group having from 2 to 6 carbon atoms, have pharmacological utility as tranquilizing and anti-emetic agents.

Methods are also known for preparing the compounds of Formula I by using, as starting materials, 1-(cyanoalkyl)-4-(2-pyrimidyl)piperazines represented by the structural formula

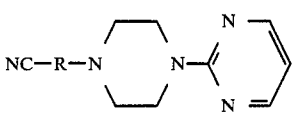

Formula II wherein R represents an alkylene group having from 1 to 5 carbon atoms. Such methods are described, for example, in U.S. Pat. Nos. 3,976,776; 3,907,801; 3,717,634; and 3,398,151, and the disclosures of these patents are hereby incorporated herein by reference.

The aforesaid patents, taken with Howard et al, *J. Org. Chem.*, Vol. 18, pp. 1484–1488 (1953) (which is referred to therein) also describe a method for preparing the compounds of Formula II. For example, for preparing 1-(3-cyanopropyl)-4-(2-pyrimidyl)piperazine, that method includes reacting piperazine with 2-chloropyrimidine to obtain 1-(2-pyrimidyl)piperazine, which is then reacted with 3-chlorobutyronitrile to obtain the desired compound.

However, such a method has a number of drawbacks. Namely, the yields are relatively poor, and the starting material, 2-chloropyrimidine, is relatively expensive. The known method, as described in the references noted above, for producing the Formula II compounds entails a considerable waste of the expensive 2-chloropyrimidine. Part of the reason for the waste is that in reacting piperazine with 2-chloropyrimidine to obtain 1-(2-pyrimidyl)piperazine, a very significant amount of by-product comprising 1,4-bis(2-pyrimidyl)-piperazine also results and must be separated out, thus wasting large amounts of 2-chloropyrimidine.

Accordingly, a need exists for alternative syntheses of the Formula II compounds which are more economical than the syntheses described in the prior art. The present invention provides such an alternative. It involves preparation of a novel 2-pyrimidyl alkanesulfonate which is then reacted with a novel cyanoalkylpiperazine.

In regard to preparation of alkanesulfonates, Crossland et al, *J. Org. Chem.*, Vol. 35, pp. 3195–3196 (1970) describes a method of preparing hydrocarbon methanesulfonates by reacting methanesulfonyl chloride with a hydroxyhydrocarbon in an inert solvent in the presence of a base, but it does not describe such a method for preparation of a heterocyclic alkanesulfonate from a hydroxyheterocycle, such as 2-hydroxypyrimidine.

It should be noted that we also have invented other alternative syntheses of Formula II compounds and have invented other novel compounds which are useful in these syntheses. These other invention are described in our co-pending U.S. patent applications, Ser. No. 407,216, filed Aug. 11, 1982, entitled "Cyanoalkylpiperazines and Methods for Their Preparation and Use" (now U.S. Pat. No. 4,515,947, issued May 7, 1985) and Ser. No. 407,215, filed Aug. 11, 1982, entitled "Acid Salts of 1-(Cyanoalkyl)-4-guanylpiperazines and Methods for Their Preparation and Use," the disclosures of which are hereby incorporated herein by reference.

SUMMARY OF THE INVENTION

The invention provides a new method (which does not involve 2-chloropyrimidine and is more cost-efficient than the prior art method) for preparing 1-(cyanoalkyl)-4-(2-pyrimidyl)piperazines. The new method includes new intermediate methods and compounds.

The new compounds of the invention are 2-pyrimidyl alkanesulfonates represented by the structural formula

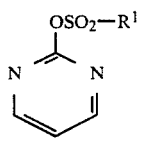

Formula III wherein $R^1$ represents an alkyl group having from 1 to 3 carbon atoms.

One of the new methods of the invention is a method for preparing a compound represented by Formula III. The method comprises reacting an acid salt of 2-hydroxypyrimidine with an alkanesulfonyl chloride represented by the structural formula

$R^1-SO_2-Cl$  Formula IV wherein $R^1$ is as previously defined, in the presence of an acid acceptor, to form a Formula III 2-pyrimidyl alkanesulfonate.

Another of the new methods of the invention is a method for preparing a 1-(cyanoalkyl)-4-(2-pyrimidyl)-piperazine represented by Formula II, starting with one of the new compounds of Formula III. The method comprises reacting a cyanoalkylpiperazine represented by the structural formula

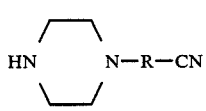

Formula V wherein R represents an alkylene group having from 1 to 5 carbon atoms, with a 2-pyrimidyl alkanesulfonate of Formula III in the presence of an acid acceptor, to form a 1-(cyanoalkyl)-4-(2-pyrimidyl)piperazine represented by the structural formula

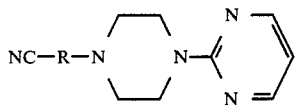

Formula II wherein R is as previously defined.

A third method of the invention comprises a sequential combination of the two new methods described above. The method is one for preparing a 1-(cyanoalkyl)-4-(2-pyrimidyl)piperazine of Formula II, starting with an acid salt of 2-hydroxypyrimidine. The method comprises reacting an acid salt of 2-hydroxypyrimidine with an alkanesulfonyl chloride of Formula IV in the presence of an acid acceptor to form a 2-pyrimidyl alkanesulfonate of Formula III and then reacting the 2-pyrimidyl alkanesulfonate with a cyanoalkylpiperazine of Formula V in the presence of an acid acceptor to form the 2-(cyanoalkyl)-4-(2-pyrimidyl)piperazine.

DESCRIPTION OF PREFERRED EMBODIMENTS

The invention is described in detail below, mainly in regard to specific preferred embodiments wherein the alkylene group represented by R in Formulas II and V is a propylene group, and the alkyl group represented by $R^1$ in Formulas III and IV is a methyl group. Those are the specific embodiments involved in producing the Formula II compound, 1-(3-cyanopropyl)-4-(2-pyrimidyl)piperazine most economically within the scope of the invention. That specific compound is most useful for ultimately producing 8-[4-[4-(2-pyrimidyl)-1-piperazinyl]butyl]-8-azaspiro[4.5]decane-7,9-dione, a compound which also has been referred to in the prior art by the name buspirone and is known to be a particularly good tranquilizing and anti-emetic agent among those of Formula I. It is a particular purpose of the invention to provide means for more cost-efficient production of buspirone. However, unless otherwise stated below, it should be understood that any discussion of general or preferred reaction conditions, reagents, optional procedures, etc. are equally applicable to the remaining embodiments within the scope of the claimed invention, wherein the alkylene group represented by R is other than propylene, and the alkyl group represented by $R^1$ is other than methyl.

Of the new compounds of the invention, represented by Formula III, a particularly preferred embodiment is 2-pyrimidyl methanesulfonate, because of its cost-efficient utility in preparing 1-(3-cyanopropyl)-4-(2-pyrimidyl)piperazine.

In accordance with a method of the invention, a Formula III compound is prepared by reacting an acid salt of 2-hydroxypyrimidine with a Formula IV alkanesulfonyl chloride in the presence of an acid acceptor under conditions sufficient to form the corresponding Formula III compound. Thus, in a particularly preferred embodiment 2-pyrimidyl methanesulfonate, i.e.,

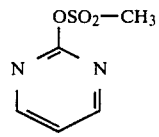

Formula VI is prepared by reacting an acid salt of 2-hydroxypyrimidine with methanesulfonyl chloride under conditions sufficient to form the Formula VI compound.

The 2-hydroxypyrimidine acid salt used in this method is easily prepared, for example, by reacting urea with tetramethoxypropane in an acidic medium. In preferred embodiments of this method 2-hydroxypyrimidine hydrochloride is used, because it is well known and easily obtained.

The method for producing 2-pyrimidyl alkanesulfonates is carried out in the presence of an acid acceptor to promote the condensation of the 2-hydroxypyrimidine acid salt with the alkanesulfonyl chloride. A typical base, such as sodium carbonate, sodium bicarbonate, potassium carbonate, potassium bicarbonate, or triethylamine, is used as the acid acceptor. Triethylamine is a preferred acid acceptor for this method.

The method for producing 2-pyrimidyl alkanesulfonates is preferably carried out in an organic solvent, inert to the reaction. A common organic solvent, such as acetone, ethyl acetate, or dichloromethane is adequate. Dichloromethane is a preferred solvent for this method.

It should be noted that some attempts to apply this method more broadly than described herein (e.g., to produce 2-pyrimidyl toluenesulfonate from toluenesulfonyl chloride) were unsuccessful.

In accordance with another method of the invention, a Formula III 2-pyrimidyl alkanesulfonate is reacted with a Formula V cyanoalkylpiperazine in the presence of an acid acceptor under conditions sufficient to form a 1-(cyanoalkyl)-4-(2-pyrimidyl)piperazine of Formula II. In a particularly preferred embodiment 2-pyrimidyl methanesulfonate is reacted with 1-(3-cyanopropyl)piperazine in the presence of an acid acceptor to form 1-(3-cyanopropyl)-4-(2-pyrimidyl)piperazine. This compound is particularly useful as a starting material for producing buspirone by the method described in the patents incorporated herein by reference above.

The Formula V cyanoalkylpiperazines used in this method are themselves novel compounds, produced by novel methods, e.g., by reaction of piperazine with a haloalkylnitrile in the presence of an acid acceptor under conditions sufficient to form the Formula V compound as the major product. A novel method of preparing a novel cyanoalkylpiperazine is described in more detail in Example 3 below. Such novel compounds and methods are also described in our copending U.S. patent application Ser. No. 407,216, filed Aug. 11, 1982, now U.S. Pat. No. 4,515,947 entitled "Cyanoalkylpiperazines and Methods for Their Preparation and Use." In that copending application we also describe methods of producing Formula II compounds by reacting Formula V cyanoalkylpiperazines with 2-halopyrimidines. It should not, however, be expected that the present method for adding a 2-pyrimidyl group to the unsubstituted ring nitrogen of a 1-(cyanoalkyl)piperazine, would work starting with a 2-pyrimidyl compound having any typical leaving group at the 2-position. For example, attempts to produce a Formula II compound in practicable yields by reacting a Formula V compound with a 2-pyrimidyl compound having a trimethylsiloxy group or a methylmercapto group at the 2-position, instead, have been unsuccessful.

The inventive method for producing Formula II compounds from compounds of Formulas III and V is carried out in the presence of an acid acceptor to promote condensation of the cyanoalkylpiperazine with the 2-pyrimidyl alkanesulfonate. If the cyanoalkylpiperazine is included in large excess, the excess amount can serve as the acid acceptor, but it is preferred instead to use one of the more common, less expensive bases, such as sodium carbonate, sodium bicarbonate, potassium carbonate, potassium bicarbonate, or triethylamine. Sodium carbonate and triethylamine are particularly preferred acid acceptors for this method.

The method for producing Formula II compounds from Formula III compounds is preferably carried out in an organic solvent, inert to the reaction. A typical organic solvent, such as toluene, acetone, xylene, or ethyl acetate is adequate. Acetone and xylene are preferred solvents.

In carrying out the reaction the 2-pyrimidyl alkanesulfonate, cyanoalkylpiperazine, and acid acceptor are brought together in the organic solvent (e.g., xylene), heated, and stirred. In order to maximize yield of the Formula II compound, it is preferable to include the cyanoalkylpiperazine and acid acceptor in amounts slightly in excess of the stoichiometric amounts for the reaction. The resulting Formula II 1-(cyanoalkyl)-4-(2-pyrimidyl)piperazine can be isolated, e.g., by washing the product solution with aqueous hydrochloric acid and then concentrating the xylene solution and adding heptane to it to precipitate the Formula II product.

In accordance with a third method of the invention, the two methods described above are carried out in sequence to produce a Formula II 1-(cyanoalkyl)-4-(2-pyrimidyl)piperazine by starting with a 2-hydroxypyrimidine acid salt. For example, in a particularly preferred embodiment of the method an acid salt of 2-hydroxypyrimidine is reacted with methanesulfonyl chloride in the presence of an acid acceptor to form 2-pyrimidyl methanesulfonate. this product is then reacted with 1-(3-cyanopropyl)piperazine in the presence of an acid acceptor to form 1-(3-cyanopropyl)-4-(2-pyrimidyl)piperazine.

All preferred conditions, reagents, etc. for the steps of the inventive method of producing Formula II compounds, starting with an acid salt of 2-hydroxypyrimidine are the same as those recited previously in the detailed description, hereinabove, of those steps as individual inventive methods.

The following Examples are presented to further illustrate some preferred embodiments of the invention.

cl EXAMPLE 1

Preparation of 2-Pyrimidyl Methanesulfonate from 2-Hydroxypyrimidine Hydrochloride A 5-liter, three-necked flask, equipped with a stirrer, thermometer and addition funnel, was charged with 2.5 L of dichloromethane and 132.5 g. (1 mole) of 2-hydroxypyrimidine hydrochloride. The resultant slurry was cooled to 5° C., and at this temperature, 348 ml. (253.0 g.; 2.5 mole) of triethylamine was added dropwise during 30 min. The resulting thick suspension was stirred at 5° C. for 15 min. and then treated at this temperature with 126 g. (1.1 mole) of methanesulfonyl chloride. The mixture was then stirred at room temperature (about 23° C.) for 18 hours and filtered to remove triethylamine hydrochloride. The remaining solid was washed with two 200 ml. portions of dichloromethane. The dichloromethane solutions were combined and washed in sequence with three 700 ml. portions of warm water (at about 40° C.), twice with 700 ml. portions of dilute hydrochloric acid (1:9), once with 700 ml. of warm water, once with 700 ml. of saturated aqueous sodium bicarbonate solution, and once with 700 ml. of warm water. The solution was dried with magnesium sulfate, decolorized with a carbon decolorizing agent, filtered and evaporated to dryness at about 23° C. The yield of solid 2-pyrimidyl methanesulfonate (melting point: 114°–120° C.) was 117.4 g. (0.674 mole; 67% yield). The structure of the product was verified by NMR, IR, and TLC analytical techniques.

EXAMPLE 2

Preparation of 2-Pyrimidyl Methanesulfonate from b 2-Hydroxypyrimidine Hydrochloride A suspension of 26.5 grams (0.2 mole) of 2-hydroxypyrimidine hydrochloride in 70 mL (50.6 grams; 0.5 mole) of triethylamine and 125 mL of dichloromethane was stirred and cooled to 10° C. To the stirred suspension was added 25.2 grams (0.22 mole) of methanesulfonyl chloride dropwise in 30 minutes holding the temperature at 10°–18° C. The mixture was stirred overnight at room temperature (about 23° C.) then washed with 120 mL of water. The product-dichloromethane layer was separated, concentrated to approximately ½ volume, and 100 mL of heptane was added. The remaining dichloromethane was distilled from the mixture to complete the precipitation of the product. The resulting 2-pyrimidyl methanesulfonate was filtered and air dried. The yield was 22.6 grams (65% of the theoretical amount) of 2-pyrimidyl methanesulfonate (melting point: 116°–120° C). The structure of the product was verified by IR and NMR analytical techniques.

EXAMPLE 3

Preparation of 1-(3-Cyanopropyl)-4-(2-pyrimidyl)piperazine from 2-Pyrimidyl Methanesulfonate A 1-liter three-necked flask, equipped with an addition funnel, stirrer and reflux condenser, was charged with 300 ml of acetone, 35.7 g. (0.288 mole) of sodium carbonate monohydrate and 100 g. (0.575 mole) of 2-pyrimidyl methanesulfonate. A solution of 79.9 g. (0.522 mole) of 1-(3-cyanopropyl)piperazine in 100 ml of acetone was added dropwise during 15 minutes to the resulting mixture, stirred at 5° C. The mixture was then refluxed for 5 hours. TLC analysis showed both starting materials in the reaction mixture. More 1-(3-cyanopropyl)piperazine (40 g.; 0.26 mole) and sodium carbonate (32.4 g.; 0.26 mole) were added, and the mixture was refluxed for 6 hours. The mixture was then cooled to room temperature and filtered. The filtrate was evaporated to give an oil, which was taken up in 500 ml of ethyl acetate. The solution was washed with two 50 ml portions of saturated aqueous sodium chloride. The washes were extracted once with 100 ml of ethyl acetate and the combined organic solutions were dried over magnesium sulfate. Removal of the solvent gave about 120 g. of a light-brown oil, which was fractionated in vacuo using a 6" column. The fraction boiling at 160°–164° C./0.20 mm Hg was collected. The yield of 1-(3-cyanopropyl)-4-(2-pyrimidyl)piperazine (melting point: 53°–56° C.) was 110.5 g. (0.478 mole; 83% yield based on 2-pyrimidyl methanesulfonate). The structure of the product was verified by NMR and IR analytical techniques.

The 1-(3-cyanopropyl)piperazine used in this Example was prepared as follows:

In a 5-liter 4-necked flask, equipped with an efficient stirrer, thermometer, condenser, and addition funnel, a slurry of 1292 g. (15.0 moles) piperazine and 930 g. (7.5 moles) sodium carbonate in 2.0 liters of ethyl acetate was stirred and heated to reflux (86° C). The heat source was removed and from the funnel 975 g. (ca. 7.5 moles) of a mixture, comprising by weight about 60% 3-chlorobutyronitrile, about 35% 3-bromobutyronitrile, and the remainder glutaronitrile, was added at such a rate that a gentle reflux was maintained. Approximately one hour was required. Gas evolution ($CO_2$) was moderate during the addition but increased subsequently. The slurry was stirred and heated until the reaction was complete.

The reaction mixture was filtered, and the resulting solid cake was pressed down under a rubber dam. The solids were washed twice by slurrying in 1-liter portions of ethyl acetate. The combined filtrates were concentrated under vacuum to remove solvent and then the bulk of the excess piperazine. Finally the pot was heated to 150°–170° C. to distill the rest of the piperazine.

The product was subsequently distilled under high vacuum to give 1-(3-cyanopropyl)piperazine (melting point: 102.5°–103.5° C.), the structure of which was verified by IR, NMR, and TLC analytical techniques. The total yield was 796 g. or 69.3% of the theoretical 1149 g. of 1-(3-cyanopropyl)piperazine.

The pot residue was found to comprise 1,4-bis(3-cyanopropyl)piperazine by-product.

EXAMPLE 4

Preparation of 1-(3-Cyanopropyl)-4-(2-pyrimidyl)piperazine from 2-Pyrimidyl Methanesulfonate To a mixture comprising 10 grams (0.057 mole) of 2-pyrimidyl methanesulfonate, 6.4 grams (0.063 mole) of triethylamine and 60 mL of xylene, was added, in one portion, 9.7 grams (0.063 mole) of 1-(3-cyanopropyl)piperazine, which was prepared as described in Example 3. The mixture was stirred and heated at 90° C. for 2 hours, then cooled to room temperature (about 23° C.). The mixture was washed with 70 mL diluted hydrochloric acid (60 mL water, 10 mL concentrated hydrochloric acid). The xylene solution layer was separated and concentrated to ½ volume at reduced pressure and 60 mL of heptane was added to precipitate the product. The product was filtered, washed with a little heptane, and air dried. The yield was 9.3 grams (70% of the theoretical amount) of 1-(3-cyanopropyl)-4-(2-pyrimidyl)piperazine (melting point: 50°–52° C.). The structure of the product was verified by NMR and IR analytical techniques.

The invention has been described in detail with particular reference to certain preferred embodiments thereof, but it will be understood that variations and modifications can be effected within the spirit and scope of the invention.

What is claimed is:

1. A 2-pyrimidyl alkanesulfonate represented by the structural formula

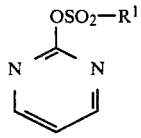

wherein $R^1$ represents an alkyl group having from 1 to 3 carbon atoms.

2. The 2-pyrimidyl alkanesulfonate of claim 1, wherein $R^1$ represents a methyl group.

* * * * *